United States Patent [19]

Sanderson

[11] Patent Number: 4,863,439
[45] Date of Patent: Sep. 5, 1989

[54] SURGICAL CANNULA

[75] Inventor: Terry L. Sanderson, Eureka, Mo.

[73] Assignee: S. Robert Kovac, St. Louis, Mo.; a part interest

[21] Appl. No.: 115,526

[22] Filed: Nov. 2, 1987

[51] Int. Cl.$^4$ .................. A61M 5/325; A61M 25/005
[52] U.S. Cl. .................................. 604/264; 604/267; 604/93; 604/902; 604/241
[58] Field of Search ................ 604/264, 267, 274, 93, 604/241, 119, 902

[56] References Cited

U.S. PATENT DOCUMENTS 3,963,028  6/1976  Cooley et al. ............... 604/902 X
4,710,180 12/1987  Johnson ....................... 604/274 X Primary Examiner—Allen M. Ostrager
Attorney, Agent, or Firm—Michael Kovac

[57] ABSTRACT

A cosmetic surgical cannula includes lightweight and less cumbersome handle means which also loosen for cleaning, but which lock securely through bonded and tight fitting engagement, as well as circumferential gripping to the surgical cannula, as disclosed.

15 Claims, 2 Drawing Sheets

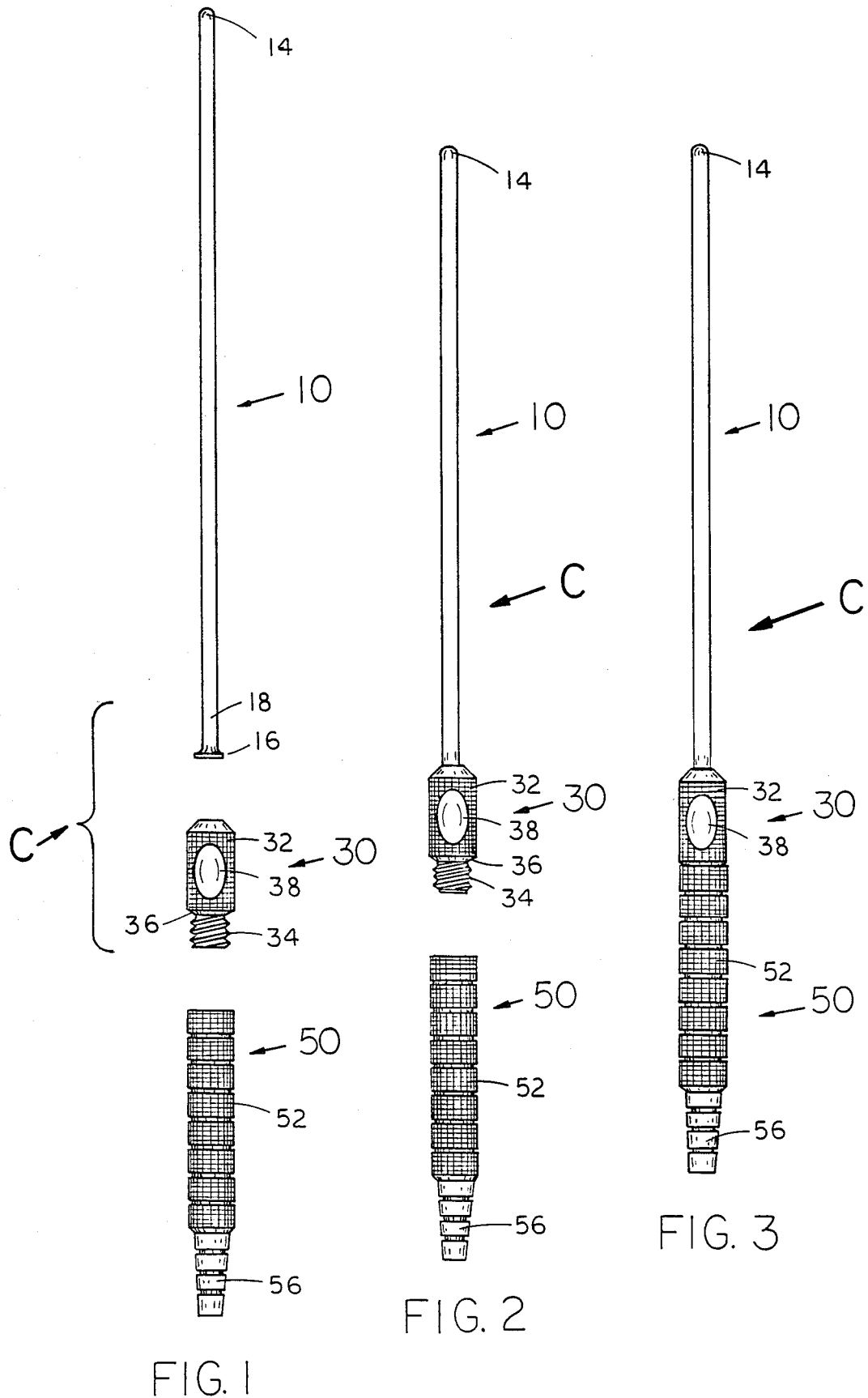

SURGICAL CANNULA

BACKGROUND OF THE INVENTION

Sedentary and over-eating habits in the Western world have produced various regimens to maintain a desired body weight and image. These include dieting, discipline, exercise and cosmetic surgery. It is known that while cosmetic surgery won't replace the benefits of dieting, discipline and exercise, it can enhance and complement those efforts. Thus, for an overall program to maintain a desired body weight and image, all of the aforementioned regimens and programs should be considered.

One of the fastest growing methods of cosmetic surgery is known as lipo-suction. Pioneered in Europe over the last decade, this procedure has become increasingly popular because it is relatively safe, effective and affordable, and unlike the other regimens and programs, it is a permanent means of removing unwanted body fat. The body does not regenerate fat cells suctioned away through this technique. Still this procedure is not for everyone because each individual case is different. Yet when warranted and performed by a skilled surgeon trained and experienced in this technique, it is an effective method of modifying body proportions to alter the silhouette.

Lipo-suction surgery involves only a small incision near the fatty area. A surgical cannula is then inserted, and fat is suctioned away through a special vacuum. Surgeons performing this procedure must not only be highly skilled in this technique, but they must possess high stamina and energy since this procedure, by necessity, requires careful, but numerous re-positioning of the cannula over a sustained period. Because of the demand for the surgeon's skill, time and energy in this procedure, the cannula has been re-designed to remove weight. This has resulted in cannulas where lighter weight plastic handles have replaced heavier weight metal cannula handles. While this has helped in providing a lighter and less cumbersome cannula, there is still a problem with current designs in that they are difficult to clean after use, thus leaving the potential for fat to remain in the cannula. When this happens, it creates an un-sterile surgical environment which, of course is unacceptable. There are various design attempts to create a cannula which can be opened for cleaning, but such designs have been less than satisfactory, and they have also not considered the need for a lightweight and long lasting product, as well. There has thus been felt a need to develop a new cannula which not only overcomes existing problems, but is also safe, effective and easy to use by the skilled surgeon.

SUMMARY OF THE INVENTION

Accordingly, it is an object of the present invention to provide a surgical cannula which is not only safe, effective and easy to use, but which can also be properly sterilized between uses.

More specifically, it is an object of the present invention to provide a surgical cannula having the multi-purpose design features of permitting opening for cleaning, providing locking of component parts when in use, facilitating manipulation by being lighter and easier to use, while also being longer lasting than all other previous designs known to date.

These and other objects and advantages of the present invention will become apparent through the provision of a surgical cannula including a hollow steel needle and first and second plastic handle members which are circumferentially mounted adjacent one end of the hollow needle. The first plastic handle member is mounted in non-rotational and non-shifting movement relative to the hollow steel needle adjacent one end thereof. Such mounting is preferably achieved through a complementary molded bonded and tight fitting joint between the first plastic handle member and the hollow steel needle. The second plastic handle is removably attached to the first plastic handle member to facilitate cleaning of the hollow steel needle and first and second plastic handle members. The construction, configuration and design of the first and second plastic handle members also provides frictional locking therebetween, while simultaneously applying circumferential and radially inwardly directed gripping pressure through the first plastic handle member to the hollow steel needle to inhibit movement thereof. In order to fix the first plastic handle member to the surgical cannula in the non-rotational and non-shifting position desired, a slightly undersized cavity is provided in the first plastic member to receive the hollow steel needle in a press fit relationship, and then the parts are assembled to one another while being relatively rotated to one another to create frictional heat therebetween to a degree sufficient to cause re-molding of the first plastic handle member circumferentially about its complementary cavity such that subsequent curing enable the first plastic handle member to form a complementary molded bonded and tight fitting joint relative to the hollow steel needle.

BRIEF DESCRIPTION OF THE DRAWINGS

FIG. 1 is an exploded top plan view showing individual components of the surgical cannula which is constructed in accordance with the teachings of the present invention;

FIG. 2 is a partially exploded top plan view similar to FIG. 1, but showing some of the components of the surgical cannula assembled to one another;

FIG. 3 is a top plan view of the surgical cannula of the present invention in which all of the components are assembled to one another to provide an interlocking design for surgical use;

Corresponding reference characters indicate corresponding parts throughout the several views of the drawings.

DESCRIPTION OF PREFERRED EMBODIMENTS

While the surgical cannula of the present invention has been primarily designed for use in connection with lipo-suction procedures as described above, it will be understood by those skilled in the art that the surgical cannula may be used for other procedures, as may be appropriate.

Figure 4:
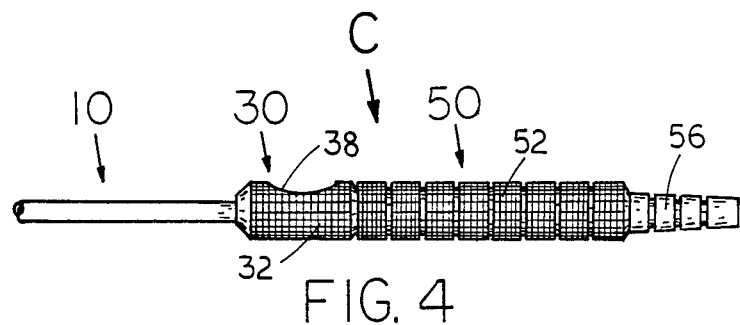
FIG. 4 is a slightly enlarged fragmentary side elevational view of the surgical cannula shown in FIG. 3.
Figure 5:
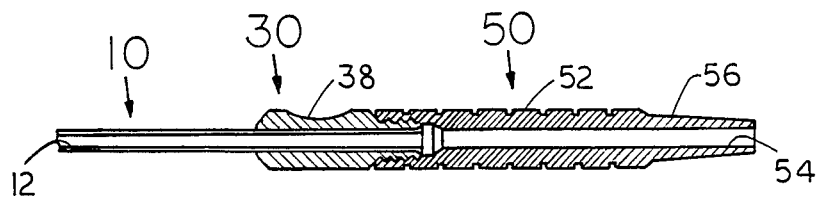
FIG. 5 is a fragmentary sectional view of the surgical cannula shown in FIG. 4.

Referring now to the drawings and first to FIGS. 1–3, it will be seen that the surgical cannula C of the present invention includes a hollow steel needle 10 having an elongated opening 12 (See FIGS. 5–7) therethrough, except at a surgical tip portion located at the frontal end thereof. Side openings (not shown) are provided at the surgical tip portion 14 to allow fat cells to be suctioned off through the elongated opening 12 thereof. At the rear end of the hollow needle 10, there is an enlarged head section 16 which is formed during assembly of components, as will be described.

A second component of the surgical cannula C of the present invention includes a ferrule or first plastic handle member 30 which is shown in FIG. 1 prior to assembly to the hollow steel needle 10. When assembled to the hollow steel needle 10, the ferrule or first plastic handle member 30 is mounted to the rear end thereof, as shown. The third component of the surgical cannula C includes a gripping or second plastic handle member 50 which can be assembled/disassembled to the first plastic handle member 30 as shown in the drawings.

In order to be useful for long service life under extreme, heavy-duty conditions, while also providing precision-engineered close tolerances in molded/machined requirements, the preferred plastic material from which the first and second plastic handle members 30, 50 are made is a polycarbonate resin, such as Lexan, which is a polycarbonate resin made by General Electric. The first and second plastic handle members 30, 50 may be molded in the final shape shown in the drawings, or may be partially molded/machined, as desired. Delrin, a DuPont acetal resin, is suitable for similar reasons.

As shown in the drawings, the first plastic handle member includes an inner larger diameter finger gripping section 32 and an outer smaller diameter male threaded section 34 which are connected to one another by a longitudinally facing wedging surface 36. An oval-shaped depression 38 is formed in the inner larger diameter finger gripping section 32 to receive the thumb of the surgeon in using the surgical cannula. The oval-depression 38, when the first plastic handle member 30 is mounted on the hollow steel needle 10, is positioned to extend transverse to the side openings (not shown) at the front end 14 of the hollow steel needle 10, in order that the side openings (not shown) will extend transverse to the skin of the patient. Thus, it is important that the first plastic handle member 30 is mounted in a non-rotational and non-shifting position on the hollow steel needle 10.

In order to achieve this mounting, the first plastic handle member 30 is formed with a complementary undersized cavity or opening 40 which extends longitudinally therethrough for receiving the hollow steel needle 10 in a press fit relationship thereto. As the hollow steel needle 10 is inserted into the complementary undersized cavity 40, the hollow steel needle 10 and the first plastic handle member 30 are rotated relative to one another to create frictional heat therebetween to a degree sufficient to cause re-molding of the plastic material circumferentially around the complementary cavity or opening 40. After curing, the plastic material circumferentially around the complementary cavity or opening 40 of the first plastic handle member forms a complementary molded bonded and tight fitting join relative to the hollow steel needle 10. To enhance the bonded and tight fitting complementary molded joint between these components, the outer surface of the hollow needle 10 may be roughenend as at 18, by sand blasting or the like.

Figure 6:
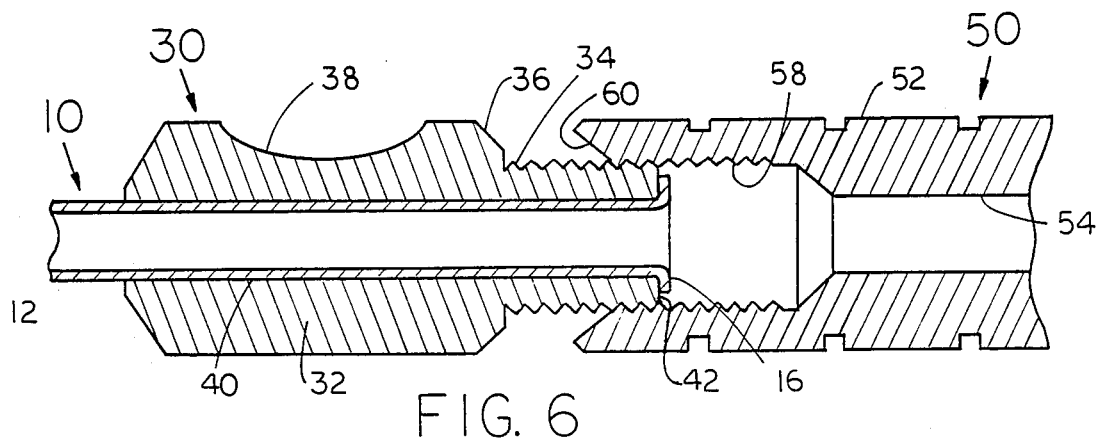
FIG. 6 is an enlarged sectional view of the surgical cannula showing the method of assembling/disassembling of handle components.
Figure 7:
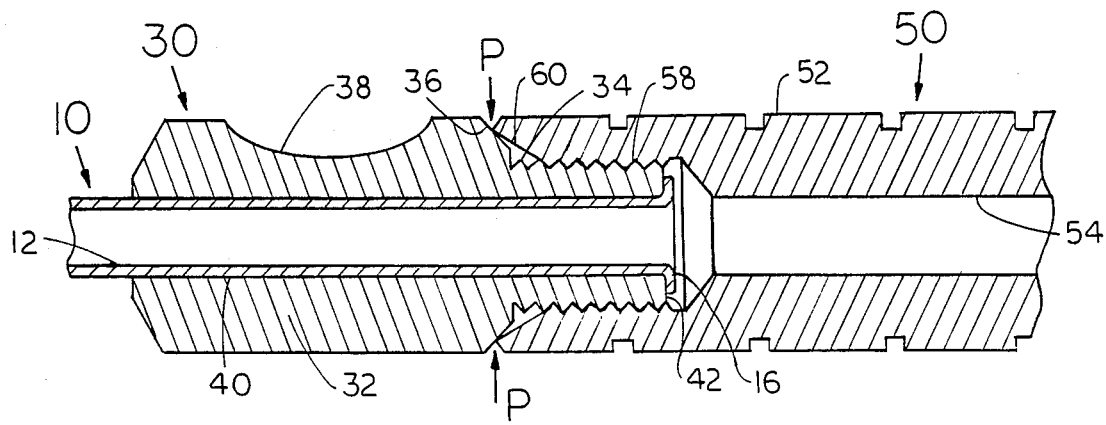
FIG. 7 is also an enlarged sectional view similar to FIG. 6 which also shows locking and gripping pressure being applied to and through the various components of the surgical cannula.

When the first plastic handle member 30 is thus assembled and mounted to the hollow steel needle 10, any shifting movement, such as by rotation or longitudinal movement of the components, is thereby prevented. This is important since the oval-depression 38 of the first plastic handle member 30 which receives the physician's thumb must always be transverse to the side openings (not shown) at the front tip 14 of the hollow steel needle 10 to avoid any possibility for skin damage due to improper postionment of the side openings (not shown). The hollow steel needle 10, after assembly to the first plastic handle member 30, may also have its rear end 16 swaged or deformed, as shown in FIGS. 6–7, to engage the rear facing surface 42 of the first plastic handle member 30. As will be appreciated, swaging or deforming the rear end 16 of the hollow steel needle 10 into an enlarged head portion which engages the rear surface 42 of the first plastic handle member 30, also assists in preventing longitudinal shifting movement of the components.

Referring now to the second plastic handle member 50, it will be seen that it has a substantially elongated shape to accomodate gripping thereof by the physician in using the surgical cannula. Preferably, the outer surface 52 of the second plastic handle member 50 has a knurled or some other type of roughened surface to enhance the physician's grip, through the remaining four fingers and palm, while the thumb is received in the oval opening 38 of the first plastic handle member 30. Similarly, the outer surface of the first plastic handle member 30 in its inner larger diameter finger gripping section 32.

The second plastic handle member 50 has an elongated passageway 54 therethrough which is in alignment with the elongated opening 12 of the hollow steel needle 12 when the components are assembled to one another. The outer free end 56 is configured to the shape of a male coupling hose fitting to receive a surgical hose thereon (not shown). The hose (not shown) is connected to a vacuum source (not shown) which draws air down the elongated opening 12 and elongated passageway 54 to allow the lipo-suction procedure, as described above, to be performed. The other end of the second plastic handle member 50 has a complementary female threaded section 58 formed in the elongated longitudinal passageway 54 thereof to receive the outer smaller diameter male threaded section 34 of the first plastic handle member 30 in threaded engagement therewith. There is also a longitudinally facing wedging surface 60 in longitudinal alignment with the wedging surface 36 of the first plastic handle member 30. Preferably, the wedging surfaces 36 and 60 do not have the same angular inclination, such that they can enhance frictional locking engagement of the first and second plastic handle members 30, 50 to one another.

Thus, as the first and second plastic handle members 30, 50 are threadably engaged with one another, as the wedging surfaces 36, 60 thereof come into contact with one another as best seen in FIGS. 6–7, the first and second plastic handle members 30, 50 will be in frictional locking engagement with one another. As will be understood by those skilled in the art, as the two non-mating wedging surfaces 36, 60 are forced into engagement, they will apply an opposing or back pressure force on the threads of the threaded sections 34, 58, thus resisting any unauthorized retrograde movement of the first and second plastic handle members 30, 50 relative to one another. It is contemplated that hand tighting pressure will, through the frictional locking engagement described above, be sufficient to prevent undesired threaded separation of the first and second plastic handle members 30, 50, until cleaning is desired. Then, by hand loosening pressure, the first and second plastic handle members 30, 50 can be threadably disassembled to facilitae cleaning thereof.

It is to be noted that as the wedging surfaces 36, 60 are forced into wedging and frictional locking engagement with one another, there is also simultaneously applied a circumferential and radially inwardly directed pressure, as indicated by the arrow P in FIG. 7. This pressure P is circumferentially and radially inwardly directed to the male threaded section 34 of the first plastic handle member 30, which deforms the plastic thereof, to also then apply a circumferential and radial gripping action on the hollow steel needle 10. This provides an additional and further locking action to inhibit rotational or logitudinal movement of the components when assembled to one another, as described above.

From the foregoing, it will be seen that the objects of this invention are achieved and other advantageous results are obtained.

As various changes could be made in the above constructions without departing from the scope of the invention, it is intended that all matter contained in the above description or shown in the accompanying drawing shall be interpreted as illustrative and not in a limiting sense.

What is claimed:

1. A surgical cannula including a hollow steel needle having an elongated opening therethrough and terminating at a surgical tip at one end thereof, a first plastic handle member circumferentially mounted on the hollow steel needle adjacent the other end thereof, a second plastic handle member removably attached to the first plastic handle member and having an elongated passageway in alignment with the elongated opening of the hollow steel needle, said second plastic handle member being removably attached from the first plastic handle member to facilitate cleaning of the hollow steel needle and the first and second plastic handle members, and means for frictionally locking the first and second plastic handle members relative to one another while simultaneously applying circumferential and radially inwardly directed gripping pressure through the first plastic handle member to the hollow steel member to inhibit relative movement thereof.

2. The surgical cannula as defined in claim 1 wherein the first plastic handle member includes additional means for longitudinal and non-rotational mounting relative to the hollow steel needle.

3. The surgical cannula as defined in claim 2 wherein said additional means includes a complementary molded bonded and tight fitting joint between the hollow steel needle and the area of the first plastic handle member circumferentially adjacent the hollow steel needle.

4. The surgical cannula as defined in claim 3 wherein said additional means further includes longitudinal stop means between the first plastic handle member and the hollow steel needle.

5. The surgical cannula as defined in claim 1 wherein the first and second plastic handle members have complementary threaded portions to permit removable attachment to one another, and cooperating wedge surfaces on said first and second plastic handle members to create frictional locking therebetween as they are moved into threaded engagement with one another while also simultaneously applying circumferential and radially inwardly directed gripping pressure through the first plastic handle member to the hollow steel needle.

6. A surgical cannula comprising a hollow steel needle having an elongated opening therethrough and terminating at a surgical tip at one end thereof, a first plastic handle member having a complementary longitudinal cavity for receiving the hollow steel needle therein at its other end, said first plastic handle member having the plastic material adjacent its complementary longitudinal cavity circumferentially and complementarily molded as a bonded and tight fitting joint relative to the hollow steel needle, said first plastic handle member also including an inner larger diameter finger gripping section and an outer smaller diameter male threaded section connected by a longitudinally facing wedging surface, and a second plastic handle member including an outer finger gripping section and an elongated passageway in alignment with the elongated opening of the hollow steel needle, one end of the second plastic handle member being configured to receive a surgical hose thereon, the other end of the second plastic handle member being a complementary female threaded section formed in the elongated longitudinal passageway thereof to receive the outer smaller diameter male threaded section therein, said second plastic handle member further being provided with a longitudinally facing outer wedging surface in longitudinal alignment with the wedging surface of the first plastic handle member, said first and second plastic handle members being threadably connected to one another to bring the aligned wedging surfaces into cooperating engagement with one another causing frictional locking engagement between the first and second plastic handle members while also simultaneously applying circumferential and radially inwardly directed pressure through the male threaded section of the first plastic handle member around the hollow steel needle.

7. A surgical cannula including a hollow steel needle having an elongated opening therethrough and terminating at a surgical tip at one end thereof, a first plastic handle member circumferentially mounted on the hollow steel needle adjacent the other end thereof, a second plastic handle member removably attached to the first plastic handle member and having an elongated passageway in alignment with the elongated opening of the hollow steel needle, and means for releasably locking the first and second plastic handle members relative to one another as said first and second plastic handle members are moved into and out of contact with one another, said first plastic handle member having a finger depression therein which is transversely aligned relative to side openings at the surgical tip of the hollow steel needle.

8. The surgical cannula as defined in claim 7 wherein the means for releasably locking the first and second plastic handle members to each other includes frictional locking means.

9. The surgical cannula as defined in claim 8 and including a complementary molded bonded and tight fitting joint between the hollow steel needle and an area of the first plastic handle member circumferentially adjacent the hollow steel needle.

10. The surgical cannula as defined in claim 8 wherein said frictional locking means comprises longitudinally aligned wedging surfaces on said first and second plastic handle members.

11. A surgical cannula including a hollow steel needle having an elongated opening therethrough and terminating at a surgical tip at one end thereof, a first plastic handle member circumferentially mounted on the hollow steel needle adjacent the other end thereof, a second plastic handle member removably attached to the first plastic handle member and having an elongated passageway in alignment with the elongated opening of the hollow steel needle, and means for releasably locking the first and second plastic handle members relative to one another as said first and second plastic handle members are moved into and out of contact with one another, said means for releasably locking said first and second plastic handle members includes frictional locking means having longitudinally aligned wedging surfaces on said first and second plastic handle members.

12. The surgical cannula as defined in claim 11 wherein the first and second plastic handle members have complementary threaded portions, and said longitudinally aligned wedging surfaces are frictionally locked together as they are moved into threaded engagement with one another.

13. The surgical cannula as defined in claim 11 wherein said longitudinally aligned wedging surfaces are configured, arranged and dimensioned to also apply circumferential and radially inwardly directed gripping pressure through the first plastic handle member to the needle.

14. The surgical cannula as defined in claim 11 wherein said first plastic handle member has a finger receiving depression therein which is transversely aligned relative to side openings at the surgical tip of the hollow steel needle.

15. The surgical cannula as defined in claim 14 wherein said second plastic handle member is complementary mounted relative to surgical tubing.

* * * * *